United States Patent

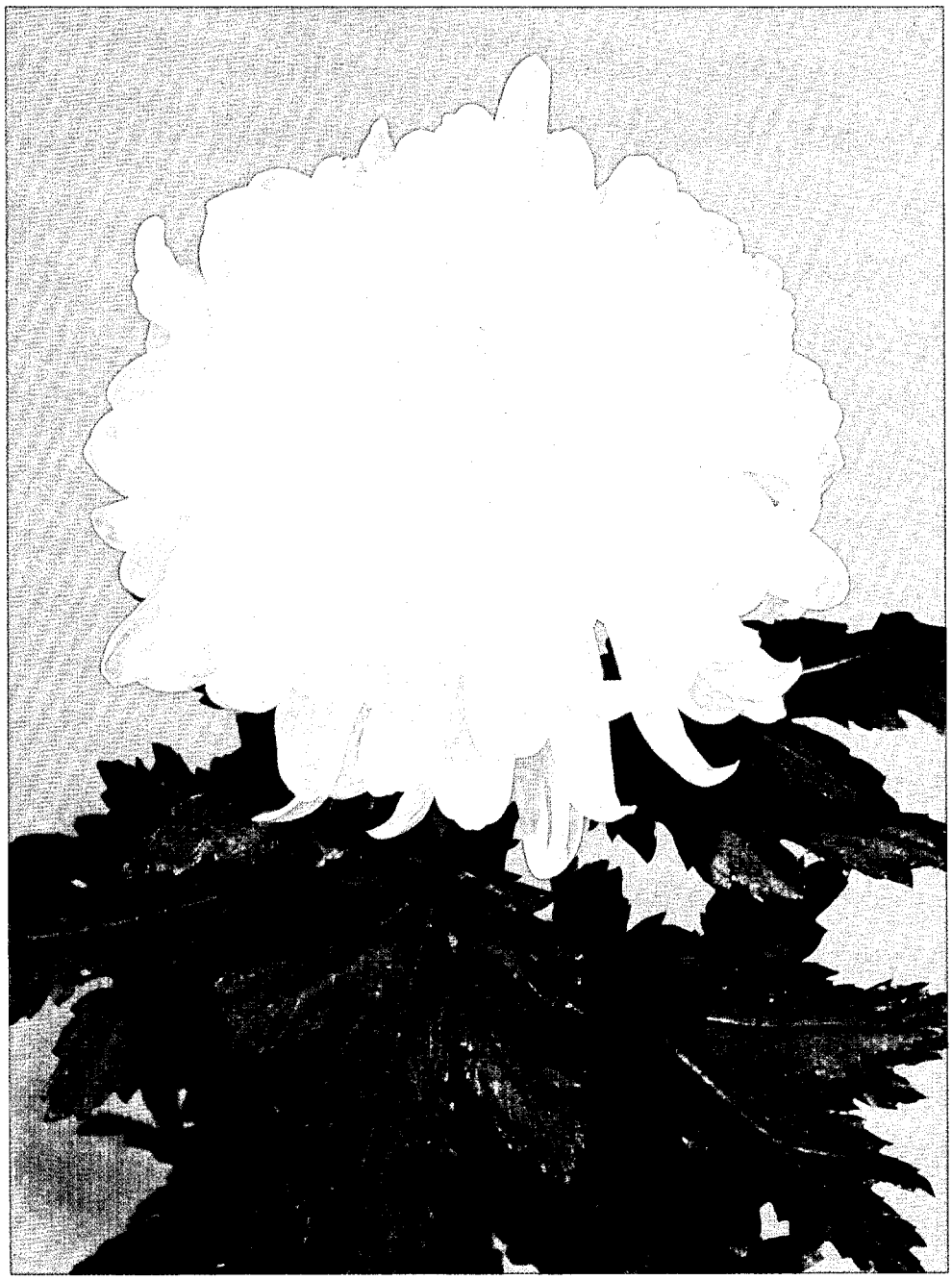

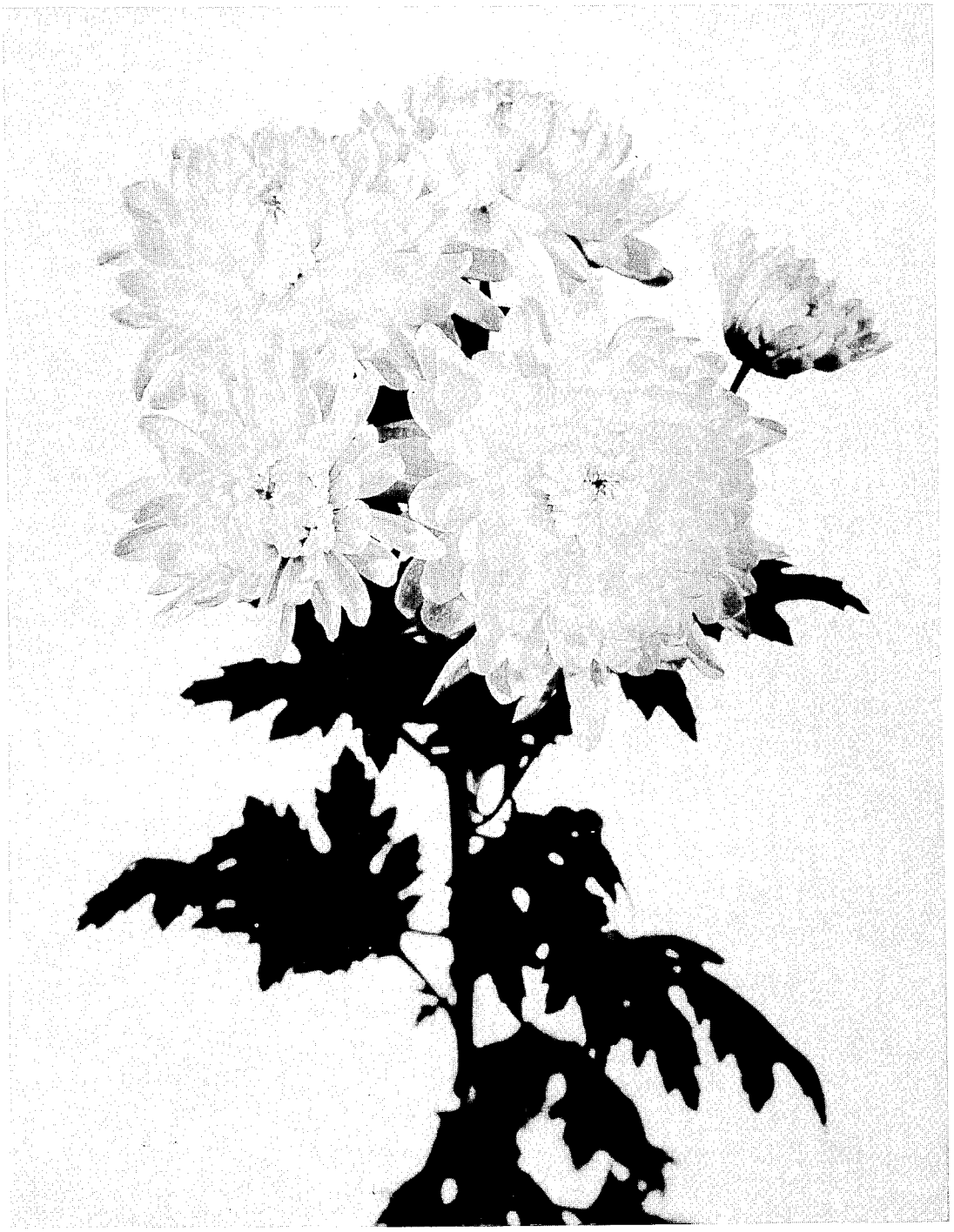

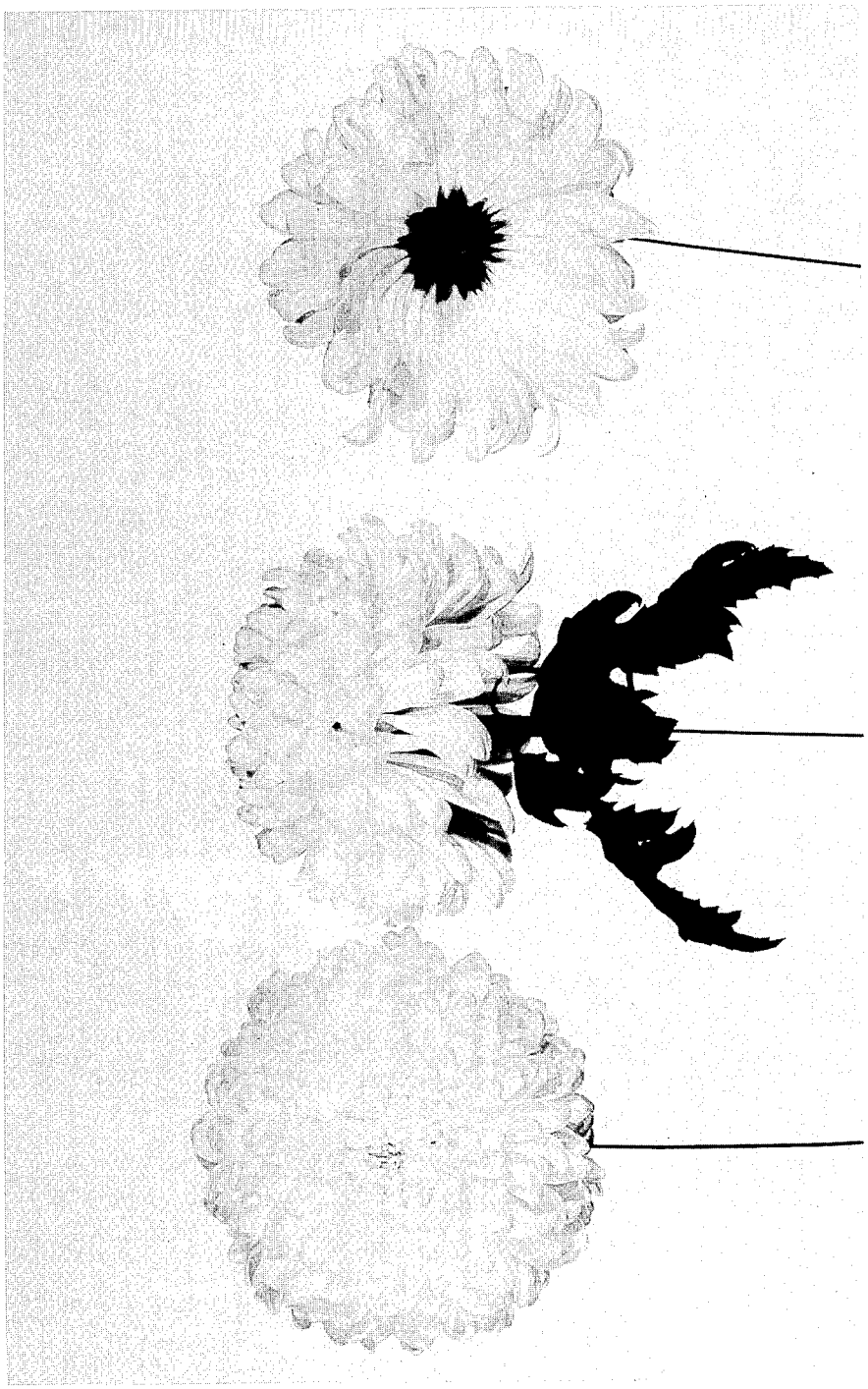

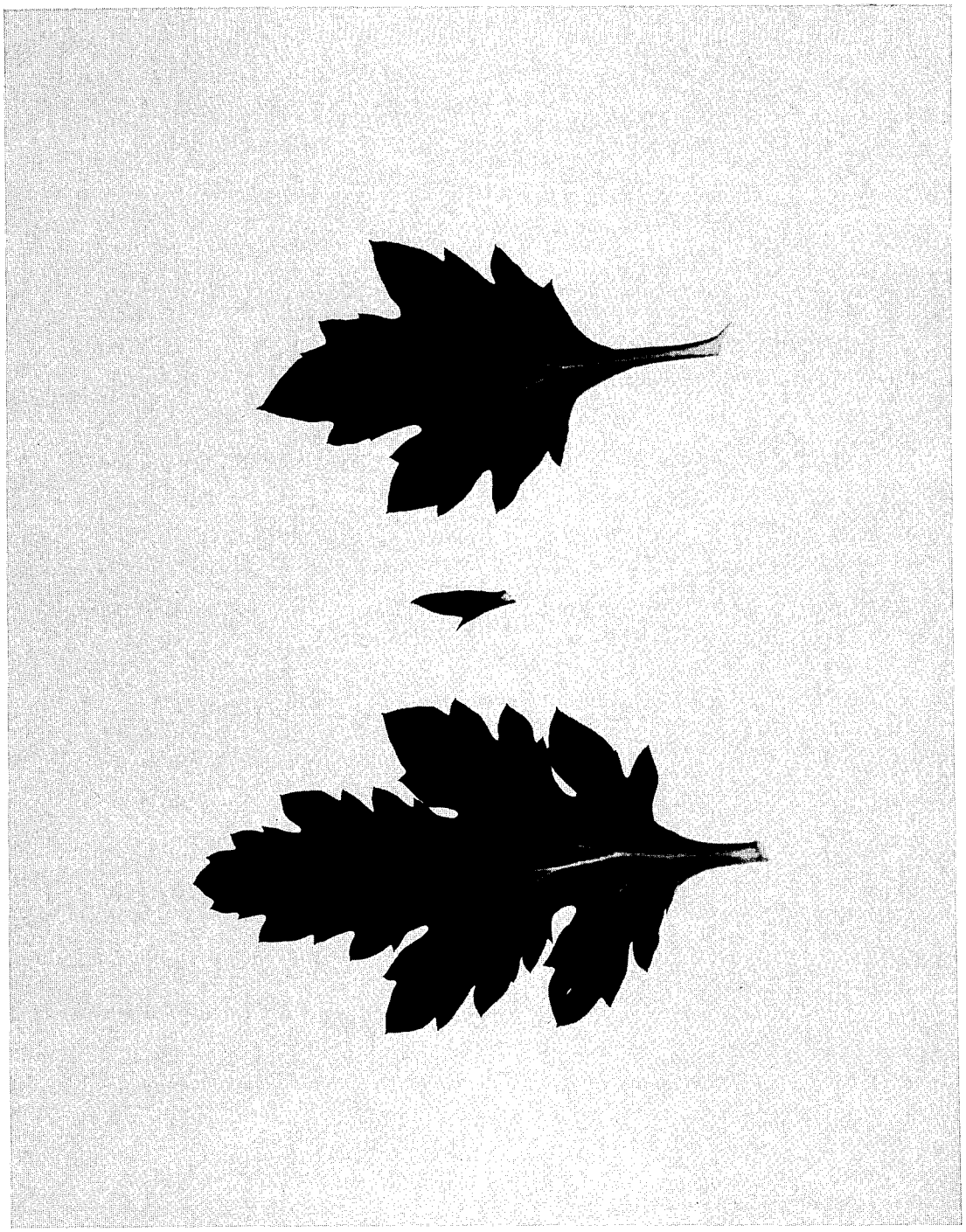

Plant Pat. 3,950

Patented Sept. 14, 1976

3,950

CHRYSANTHEMUM PLANT

Walter H. Jessel, Jr., Doylestown, and William E. Duffett, Akron, Ohio, assignors to Yoder Brothers, Inc., Barberton, Ohio

Filed Aug. 27, 1975, Ser. No. 608,257

Int. Cl.[2] A01H *5/00*

U.S. Cl. Plt.—77 1 Claim

The present invention comprises a new and distinct cultivar of *Chrysanthemum morifolium,* Ramat., hereinafter referred to by the cultivar name Palisade (#70269012).

Palisade is a product of a planned breeding program which had the objective of creating new cultivars with standard type inflorescence, uniform nine week response, large inflorescence size, excellent shipping durability, and with the ability to produce commercially acceptable quality during high light and high temperature periods. These traits in combination were not present in previously available commercial cultivars.

Palisade was originated from a cross made in a controlled breeding program in Barberton, Ohio in the year 1969. The female, or seed parent, was Snowdon #21660E01; unpatented; commercially available), a white standard of parentage unknown to the present inventors. The male, or pollen parent, was #67016999 (unnamed seedling), a white standard originated by the present inventors from a cross between #63820002 (unnamed seedling) and #21610E01 (unnamed seedling).

Palisade was discovered and selected as a flowering plant within the progeny of the stated cross by William E. Duffett and Walter H. Jessel, Jr. on Nov. 17, 1970 in a controlled environment in Barberton, Ohio.

The first act of asexual reproduction of Palisade was accomplished when vegetative cuttings were taken from the initial selection in February 1971 in a controlled environment in Barberton, Ohio by a technician working under formulations established and supervised by William E. Duffett and Walter H. Jessel, Jr. Horticultural examination of selected units initiated Jan. 11, 1972 has demonstrated that the combination of characteristics as herein disclosed for Palisade are firmly fixed and are retained through successive generations of asexual reproduction.

Palisade has not been observed under all possible environments. The phenotype may vary significantly with variations in environment such as temperature, light intensity, and daylength. The following observations, measurements, and comparisons describe single stem disbud and single stem spray plants grown in a greenhouse in Barberton, Ohio under environmental conditions which closely approximate those generally used in commercial practice, as described in Chart A and Chart B which appear at the end of the present specification.

The following traits have been repeatedly observed and are determined to be basic characteristics of Palisade which in combination distinguish this chrysanthemum as a new and distinct cultivar:

(1) Standard (disbud) to decorative (spray) inflorescence type.
(2) Semi-incurve (disbud) to flat (spray) inflorescence form.
(3) White inflorescence color.
(4) Diameter across face of inflorescence from 3.5 to 4.5 inches (spray) and from 5.0 to 6.5 inches (disbud) at maturity.
(5) Uniform nine week (disbud) and ten week (spray) flowering response.
(6) Tall plant height.
(7) Upright branching pattern.
(8) Good shipping durability.

(9) High grade-out (Society of American Florists Standards).

The accompanying photographic drawings show typical inflorescence and foliage characteristics of Palisade, with colors being as nearly true as possible with illustrations of this type. Sheet 1 is a color photograph of Palisade as a cut disbud. Sheet 2 is a black and white photograph of Palisade as a cut spray. Sheet 3 is a black and white photograph showing three views of the infloresence of Palisade. Sheet 4 is a black and white photograph showing the foliage of Palisade at three stages of growth.

Of the many commercial cultivars known to the present inventors, the most similar existing cultivars for use as a cut disbud are Nob Hill (#21580E04; unpatented, Colonel Comfort (#63868C01; U.S. Plant Pat. #3,605), Dignity (#21700E01; U.S. Plant Pat. #3,309), and the maternal cultivar, Snowdon. Reference is made to the attached Chart C which compares certain characteristics of the above mentioned cultivars with the same characteristics of Palisade. General comparisons are as follows:

(1) In comparison to Nob Hill, Palisade has whiter inflorescence color, less tendency to bruise when packed for shipping, taller plant height, shorter flowering response period, and less incurved inflorescence form. The diameter across face of inflorescence, branching pattern, and inflorescence type of Palisade are similar to those of Nob Hill.

(2) In comparison to Colonel Comfort, Palisade has whiter inflorescence color, smaller diameter across face of inflorescence, and shorter plant height. The durability of inflorescence when packed for shipping, branching pattern, flowering response period, and inflorescence form and type of Palisade are similar to those of Colonel Comfort.

(3) In comparison to Dignity, Palisade has greater tendency to bruise when packed for shipping and shorter plant height. The inflorescence color, diameter across face of inflorescence, branching pattern, flowering response period, inflorescence form, and inflorescence type of Palisade are similar to those of Dignity.

(4) In comparison to Snowdon, Palisade has greater diameter across face of inflorescence, less tendency to bruise when packed for shipping, and taller plant height. The inflorescence color, branching pattern, flowering response period, inflorescence form, and inflorescence type of Palisade are the same as those of Snowdon.

Of the many commercial cultivars known to the present inventors, the most similar existing cultivars for use as a cut spray are Polaris (#21660E04; unpatented), Icecap (#541833–4; unpatented), and the material cultivar, Snowdon. Reference is made to attached Chart D which compares certain characteristics of the above mentioned cultivars with the same characteristics of Palisade. General comparisons are as follows:

(1) In comparison to Polaris, Palisade has whiter inflorescence color, greater diameter across face of inflorescence, shorter plant height, higher grade-out (SAF standards), and longer flowering response period. The inflorescence form and inflorescence type of Palisade are the same as those of Polaris.

(2) In comparison to Snowdon, Palisade has greater diameter across face of inflorescence, taller plant height, and less incurved inflorescence form. The inflorescence color, grade-out (SAF standards), flowering response period, and inflorescence type of Palisade are the same as those of Snowdon.

(3) In comparison to Icecap, Palisade has greater diameter across face of inflorescence, higher grade-out (SAF standards), shorter flowering response period, and different inflorescence type. The inflorescence color, plant height, and inflorescence form of Palisade are the same as those of Icecap.

In the following description, color references are made to The Munsell Limit Color Cascade, 1972 edition. The color values were determined between 8:00 and 8:30 a.m. on Feb. 6, 1975 under 150 foot-candle light intensity at Barberton, Ohio.

BONTANICAL CLASSIFICATION

*Chrysanthemum morifolium*, Ramat., cv Palisade.

I. Inflorescence

A. Capitulum:

*Form.*—Semi-incurved (disbud) to flat (spray).

*Type*—Standard (disbud) to decorative (spray).

*Permanence.*—14–18 days.

*Diameter across face.*—3.5 to 4.5 inches (spray) and 5.0 to 6.5 inches (disbud).

B. Corolla of ray florets:

*Texture (adaxial).*—Glabrous.

*Appearance and form.*—Ligulate.

*Arrangement.*—Whorled on receptacle.

*Persistence.*—Resists shatter.

*Color (abaxial).*—22–2 to white.

*Color (adaxial).*—22–2 to white.

C. Reproductive organs:

*Androecium.*—Scant; present disc florets only; syngenesious stamen; scant pollen.

*Gynoecium.*—Present both ray and disc florets; inferior, bicarpellate ovary; single style; two-lobed stigma.

II. Plant

A. General appearance: Upright; tall height.

B. Duration and texture: Perennial; herbaceous.

C. Foliage:

*Color (abaxial).*—20–15 to 20–12.

*Color (adaxial).*—20–11, but more greyed.

*Shape.*—Spatulate; deeply lobed.

*Texture.*—Glabrous.

*Arrangement.*—Alternate.

*Veination.*—Prominent.

*Margin.*—Moderately serrated.

CHART A—AVERAGE GREENHOUSE CHRYSANTHEMUM ENVIRONMENTS USED FOR BARBERTON, OHIO

| Season | Temperatures used (°F.) Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: on, 5:30 p.m.; off, 7:30 a.m. | From Oct. 15: 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m.; off, 7:30 a.m. | To Apr. 15: 300 p.p.m. |
| Summer | 62 to 68 | 70 to 90 | 65 to 75 | 1 to 2 weeks at 3 hours per night of 7–10 f.c. | One 6:00 p.m.; off, 8:00 a.m. | None. |

NOTE.—For intensity of direct solar radiation, refer to Chart B.

CHART B

INTENSITY OF DIRECT SOLAR RADIATION

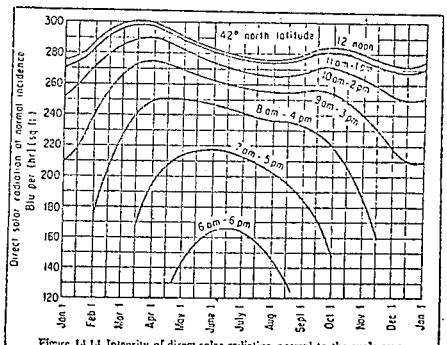

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C—COMPARISON OF PALISADE, NOB HILL, COLONEL COMFORT, DIGNITY AND SNOWDON

| Cultivar | Inflorescence color | Diameter across face of inflorescence (inches) | Tolerance of shipping | Plant height | Branching pattern | Flowering response period (weeks) | Inflorescence form and type |
|---|---|---|---|---|---|---|---|
| Palisade | White | 5 to 6½ | Good | Tall | Upright | 9 | Semi-incurved standard. |
| Nob Hill | Ivory white | 5 to 6½ | Poor | Medium | do | 10 | Incurved standard. |
| Colonel comfort | do | 6½ to 7½ | Good | Very tall | do | 9 | Semi-incurved standard. |
| Dignity | White | 5 to 6½ | Excellent | do | do | 9 | Do. |
| Snowdon | do | 4½ to 6 | Poor | Medium | do | 9 | Do. |

NOTE.—Comparisons made of plants grown as a cut disbud in a greenhouse in Barberton, Ohio under conditions as described in Chart A and Chart B.

CHART D—COMPARISON OF PALISADE, POLARIS, SNOWDON AND ICECAP

| Cultivar | Inflorescence color | Diameter across face of inflorescence (inches) | Plant height | Gradeout (SAF standards) | Flowering response period (weeks) | Inflorescence form and type |
|---|---|---|---|---|---|---|
| Palisade | White | 3.5 to 4.5 | Tall | Good | 10 | Flat decorative. |
| Polaris | Ivory white | 3.25 to 3.50 | Very tall | Poor | 9 | Do. |
| Snowdon | White | 3.0 to 4.0 | Medium | Good | 10 | Semi-incurved decorative. |
| Icecap | do | 2.5 to 2.75 | Tall | Poor | 11 | Flat pompon. |

NOTE.—Comparisons made of plants grown as a cut spray in a greenhouse in Barberton, Ohio under conditions as described in Chart A and Chart B.

We claim:

1. A new and distinct cultivar of chrysanthemum plant known by the cultivar name Palisade and particularly characterized as to uniqueness by the combined characteristics of standard (disbud) to decorative (spray) inflorescence type; semi-incurve (disbud) to flat (spray) inflorescence form; white inflorescence color; diameter across face of inflorescence from 3.5 to 4.5 inches (spray) and from 5.0 to 6.5 inches (disbud) at maturity; uniform nine week (disbud) and ten week (spray) flowering response; tall plant height; upright branching pattern; good shipping durability; and high gradeout (Society of American Florists Standards).

No references cited.

ROBERT E. BAGWILL, Primary Examiner